May 21, 1963 P. ECKE Plant Pat. 2,260
POINSETTIA PLANT
Filed Oct. 23, 1961
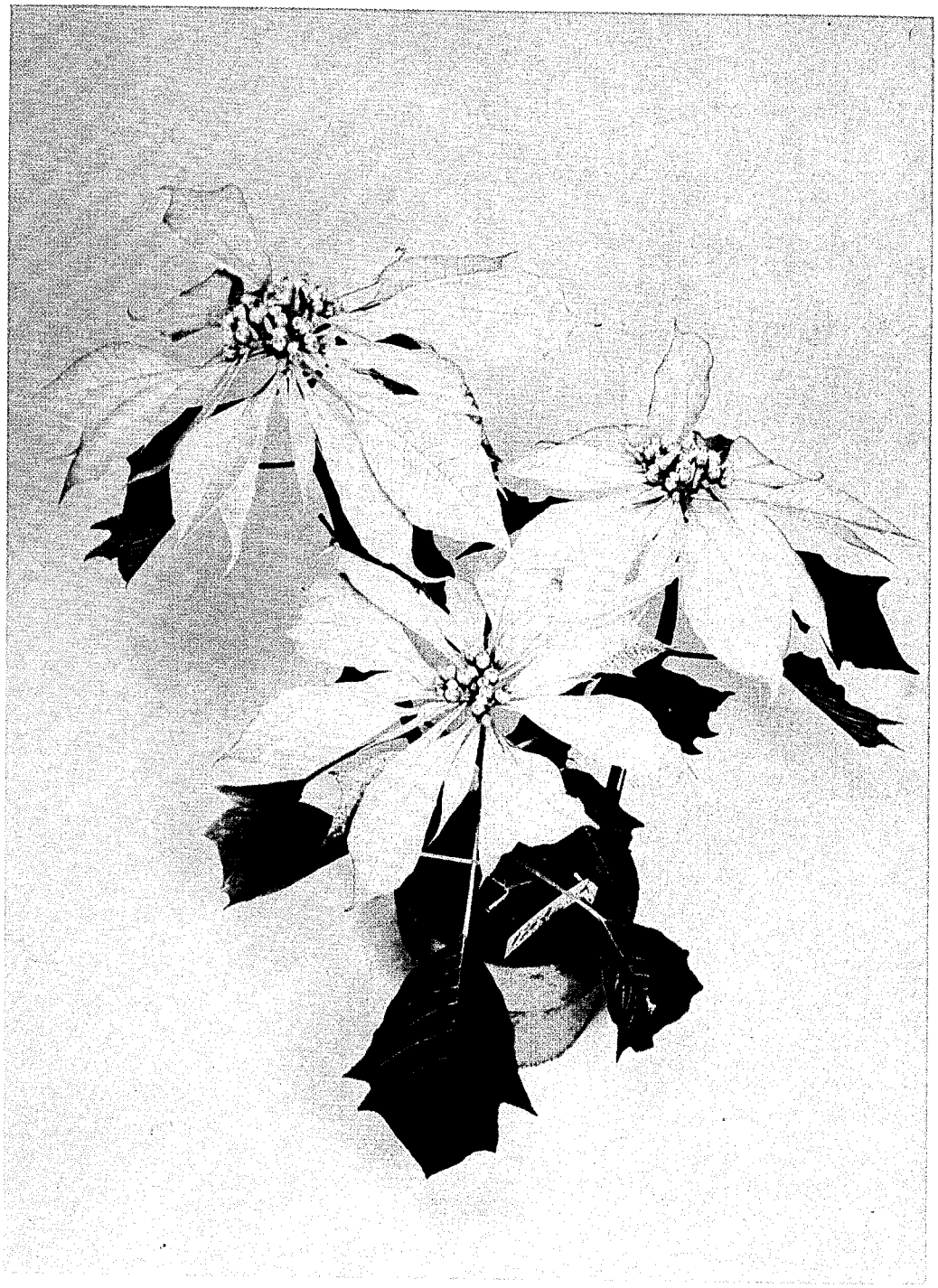
INVENTOR
Paul Ecke
by Wm. S. Graham
Attorney United States Patent Office Plant Pat. 2,260
Patented May 21, 1963

2,260
POINSETTIA PLANT

Paul Ecke, P.O. Box 488, Encinitas, Calif.
Filed Oct. 23, 1961, Ser. No. 147,113
1 Claim. (Cl. 47—60)

The subject of the present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly by the unusual pale pink color of its bracts, as well as longer and wider bracts, the petioles of which are unusually short for a pink variety, which contract the open center of the bract involucre around an abundant, closely centered, inflorescence. This new variety is characterized also by an unusually strong and stiff peduncle, which is resistant to breakage in handling and shipment.

The accompanying illustration, forming a part of this application, graphically shows this new variety in color at substantially full maturity or optimum, the illustration being a perspective view taken from an angle above the plant and therefore illustrating the bracts and foliage leaves substantially as a full face view.

The colors referred to herein correspond approximately with those shown in "Dictionary of Color" by Maerz & Paul (first edition, 1930) and identified by the common color names and by the plate of said color standards, as recapitulated in tubular form herein.

The following description more fully sets forth the characteristics of this new variety.

*Parentage*

This new variety was originated, discovered and cultivated by me in a cultivated area of the glass house at my experimental and growing gardens at Encinitas, California, by cuttings. It originated as a cultivated sport of poinsettia plant of the variety commonly called "Barbara Ecke Supreme," which is a patented variety, well known in the trade by that name, and patented in my Plant Patent No. 1,055, dated December 18, 1951.

*Propagation*

This new variety of poinsettia plant has been asexually reproduced and cultivated by me in my said glass house by cuttings, and successive reproductions thereof have remained true to type, and it has shown its herein described qualities and characteristics to be permanently fixed. In asexually reproducing the new variety, I found it satisfactory and efficient to cut pieces of stalk of softwood substantially six inches in length in or about the months of June, July and August and to set one end of such cuttings in beds of sand in my glass house. After three or four weeks, the cuttings are well rooted and may be transferred to individual pots. My experience has been that the optimum temperature for growing this new variety under glass ranges from 62 to 65 degrees F., night temperature, the daytime temperature being warmer, such as 70 to 75 degrees F., and subject to the varying conditions of light, heat, thickness of glass, cultivation, character of soil, fertilizer, and pruning or pinching.

*Habits of Growth*

This new variety of poinsettia plant develops its growth at just about the usual normal rate for average growth of poinsettia plants and will mature to optimum from about December 5th to 20th and produces the optimum of its bract involucre in that period of time. The bracts hold quite tenaciously in the involucre and, because they are of a relatively thick and fleshy type, do not dry out or crinkle, frequently remaining in prime optimum condition for three to four weeks. This new variety is hardy and healthy in growth and seems to have an unusual resistance to disease and other detrimental factors and influences. Its resistance to cold temperatures is substantially average, and not exceptional.

More particularly, this new variety is unusually resistant to a stem rot disease condition which is usually recognized as being caused by a root fungus designated rhizoctonia, and is also unusually resistant to a root rot condition caused by a fungus thielaviopsis, the detrimental factors of which are principally evidenced by leaf-drop of the foliage prior to complete maturity of the bract involucre and inflorescence. This resistance to disease and detrimental factors has been observed in this new variety when it has been grown side by side with other existing known varieties in the same field or in the same greenhouse condition, and the comparison of the new variety with known varieties has been observed over several years. These stated advantages of this new variety were established by observation of conditions present under usual and normal southern California field culture conditions in which night-time temperatures in winter frequently go down into the lower forties (F.). In plants grown in the greenhouse the temperature is maintained substantially uniformly around sixty to sixty-five degrees (F.), and the same conditions would not be so readily observable as under field grown conditions and comparisons.

*Structure*

This new variety has a well-developed spread of root structure. The peduncle or main stalk is of a medium dark brownish green color and of stiff and sturdy structure. Its normal average height is about 3 to 4 feet, developing the lesser height under cultivation out of doors. The internode space between foliage leaves is quite uniform and regular. At the upper free terminal or axial end of the peduncle, a node is formed from which grow pale green, closely grouped, short branches or stemlike spurs, which bear the bract involucre and a closely centered inflorescence. The bracts are unusually long and wide for a pink variety, and the petioles thereof are unusually short, which draws the bracts inwardly to a more closely centered relation around the inflorescence.

*Bracts*

In the usual pink varieties of poinsettia plants, the petioles of the bracts are quite long, and the bracts are relatively short and narrow, thereby providing a wide-open center to the involucre; whereas, in this present new variety, the bracts are unusually long and wide, and the petioles are relatively short for a pink variety, and thus cluster the involucre of bracts closely around the inflorescence. The bracts are also spread in a single layer of bracts, radiating as a wreath with very little overlapping of edges of relatively next adjacent bracts.

The bracts are of varying shades of relatively lighter, medium and darker tones of a pale rose pink color of brilliant hue, the pale lighter tones and the medium tones of the bracts predominating, and the darker toned bracts being relatively few, so that the involucre as an entirety has a brilliant delicate pale rose-pink appearance, decidedly more pale in tint-tone and of less color-depth than known pink varieties. The bracts vary in size, both in length and width, but are both wider and longer than the bracts of known pink varieties of poinsettia plants. Also, the bracts have an irregularity of shape but are generally and predominantly prolately ovate-acuminate.

*Foliage Leaves*

The foliage leaves are arranged around the peduncle, the nodes thereof being quite uniformly spaced, and the petioles radiate from the peduncles in stepped, staggered order. The foliage leaves are of a dark green color, and the venation thereof is of the herring-bone type. The shape of the foliage leaves is a modified oak-leaf type, generally oblate-ovate at the base portion and scalloped with modified oak-leaf points at the outer end portion. As is not uncommon in poinsettia plants, one or two of the foliage leaves adjacent the bract involucre may, but not always, be tinted with a modified hue of color somewhat resembling the color of the bracts; but this is not a distinguishing fixed characteristic of this new variety and may or may not occur in different plants.

*Inflorescence*

The inflorescence grows upon the pale green branches or spurs heretofore described as branching from the free axial end of the peduncle and centrally of the bract involucre. The flowers of this inflorescence are closely grouped and are prominent at the center of the involucre and, to a large extent, fill the relatively small open center of the bract involucre. Upon the spur length branches grow the flowers. As in a large number of varieties of poinsettia plants, the cyathium is of pale green color, small and not prominent, and the flower growing therefrom is orange yellow in color with a touch of crimson red center.

*Variations*

Different plants of this variety have an unusual similarity of adherence to characteristics and type herein described. However, there may be some variation in the characteristics of minor details, in comparison of plants growing in various localities, in different soils, and at different times of the year, varying temperatures, varying types of glass house, or out of doors.

*Color Tabulation*

The color designations according to the color plates of said "Dictionary of Color" are recapitulated in tabular form as follows:

| Part of plant | Common name of color | Dictionary of color | | |
|---|---|---|---|---|
| | | Plate | Letter | Number |
| Peduncle | Dark brownish green | 16 | L | 8 |
| Stemlike spurs which bear the inflorescence. | Pale green | 18 | K | 6 |
| Bracts | Varying shades of relatively lighter, medium and darker tones of pale rose pink of brilliant hue: | | | |
| | (a) Bracts of lighter tone. | 1 | D | 5 |
| | (b) Bracts of medium tone. | 1 | J | 5 |
| | (c) Bracts of darker tone. | 2 | L | 6 |
| Foliage leaves | Dark green | 32 | H | 7 |
| INFLORESCENCE | | | | |
| Cyathium | Pale green | 18 | K | 6 |
| Flowers | Orange yellow | 10 | J | 4 |
| Center of flowers | Crimson red | 49 | K | 3 |

Having described and illustrated my new variety of poinsettia plant, I claim:

A new and distinct variety of poinsettia plant substantially as illustrated and described, characterized by a bract involucre of pale, delicately toned, rose-pink color of brilliant hue in which the bracts have varying tones of said rose-pink color, with the bracts of the darker shades being relatively few in number, whereby the involucre as an entirety has a pale rose-pink ocular effect, lighter in tone than that of known pink varieties, the bracts being wider and longer than in known pink varieties and of generally prolately ovate-acuminate shape, said bracts being of the thick, fleshy type, and growing on relatively short petioles, whereby they are closely centered and radiate from the inflorescence in a wreath of a single layer of radiating bracts, the inflorescence at the center of the bract involucre being prominent and closely grouped, and said plant being further characterized by a stiff and sturdy peduncle.

No references cited.